United States Patent [19]

Takeuchi et al.

[11] Patent Number: 5,021,549

[45] Date of Patent: Jun. 4, 1991

[54] PHYSIOLOGICALLY ACTIVE SUBSTANCES, PROBESTIN AND PROSTATIN AND PRODUCTION THEREOF

[75] Inventors: Tomio Takeuchi, Tokyo; Takaaki Aoyagi, Fujisawa; Masa Hamada, Tokyo; Hiroshi Naganawa, Tokyo; Shigemi Yoshida, Tokyo, all of Japan

[73] Assignee: Zaidan Hojin Biseibutsu Kagaku Kenkyu Kai, Tokyo, Japan

[21] Appl. No.: 232,852

[22] Filed: Aug. 16, 1988

[30] Foreign Application Priority Data

Sep. 28, 1987 [JP] Japan ................................ 62-240600

[51] Int. Cl.$^5$ ............................ C07K 5/08; C07K 5/10
[52] U.S. Cl. ...................................... 530/330; 530/331

[58] Field of Search ................................ 530/330, 331

[56] References Cited

U.S. PATENT DOCUMENTS 4,719,200  1/1988  Eguchi et al. ...................... 530/331

Primary Examiner—Lester L. Lee
Attorney, Agent, or Firm—Larson and Taylor

[57] ABSTRACT

New physiologically active substances, named probestin and prostatin, respectively, are produced from a new microorganism, *Streptomyces azureus* MH663-2F6 strain identified as FERM P-9541 or FERM BP-1963. Probestin and prostatin have an activity inhibitory to aminopeptidase M and also have immunopotentiating properties.

3 Claims, 4 Drawing Sheets

PHYSIOLOGICALLY ACTIVE SUBSTANCES, PROBESTIN AND PROSTATIN AND PRODUCTION THEREOF

SUMMARY OF THE INVENTION

This invention relates to new physiologically active substances which are respectively named probestin and prostatin, each having an activity inhibitory to aminopeptidase M and also having an immunopotentiating property. This invention also relates to processes for the production of probestin and prostatin.

BACKGROUND OF THE INVENTION

It is known that a variety of physiologically active substances are produced by microorganisms and that a Streptomyces strain designated or identified as NCIB 8845 or ATCC No. 14903 produces an antibiotic named actinonin which exhibits an activity inhibitory to aminopeptidase M as well as an immunopotentiating activity [See U.S. Pat. No. 3,240,787 and Umezawa et al., "The Journal of Antibiotics," vol. 38, p. 1629-1630 (1985)]. The activity of actinonin inhibitory to aminopeptidase M is not so strong that its $IC_{50}$ value against aminopeptidase M is 0.40 µ/ml. Thus, there remains a need for an inhibitory agent which is more active than actinonin against aminopeptidase M and which is useful in immunological therapeutic treatment of various diseases in mammalian animals, including men.

An object of this invention is to provide new compounds which are useful as the immunopotentiator. A further object of this invention is to provide processes for the fermentative production of these new compounds.

We, the present inventors, have made extensively our research in an attempt to produce and provide new physiologically active compounds which have a higher activity inhibitory to aminopeptidase M. As a result, we have now found that when a new strain of the genus Streptomyces which was allotted a laboratory designation MH663-2F6 is cultivated in a culture medium, there are produced and accumulated in the culture such new two substances which show the activities inhibitory to aminopeptidase M. We have succeeded in isolation of these two substances and in purification of them. From the chemical, physical and biological studies of these isolated two substances, it has been confirmed that each of these substances is a new compound which is less toxic and which is distinguishable from any of the known compounds. Thus, we have nominated these two new compounds as probestin and prostatin, respectively. Probestin and prostatin have the following chemical structures;

Probestin:

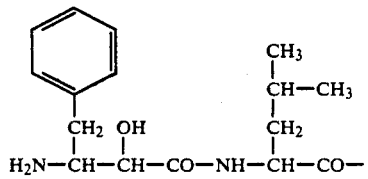

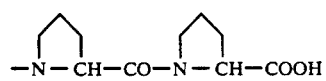

Prostatin:

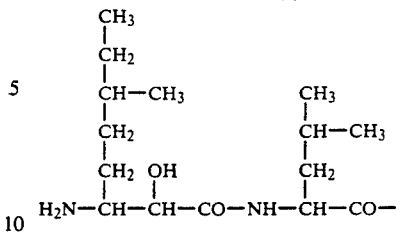

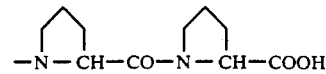

DETAILED DESCRIPTION OF THE INVENTION

According to the first aspect of this invention, therefore, there are provided the new physiologically active compounds, probestin and prostatin, which are represented by the following general formula;

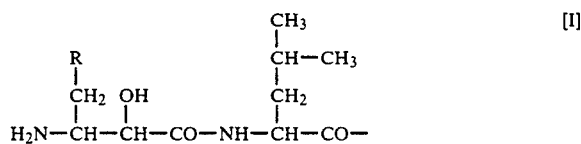

wherein R denotes a phenyl group for probestin, or R denotes a 2-methyl-butyl group for prostatin, or a pharmaceutically acceptable salt thereof.

Figure 1:
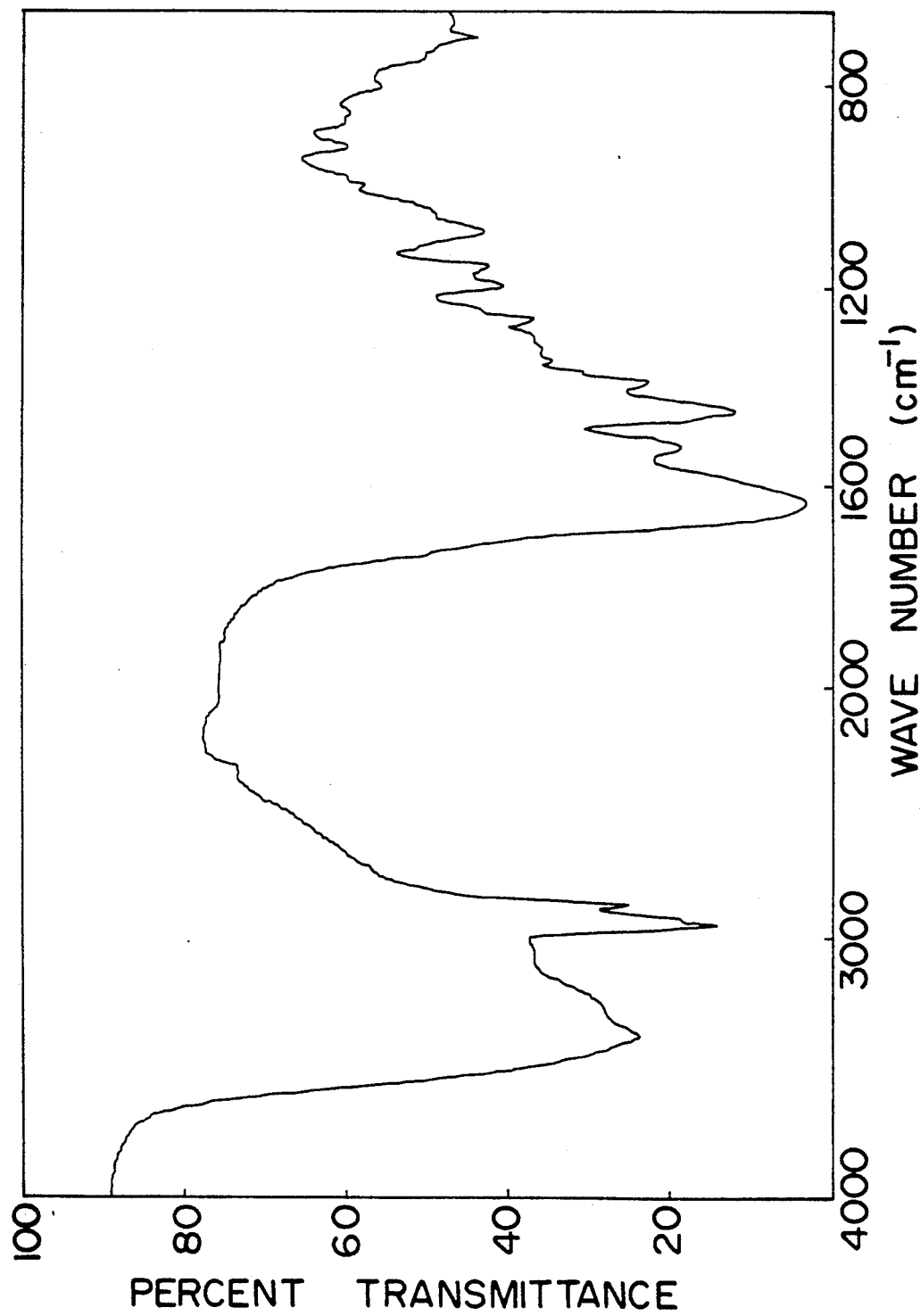
Figure 2:
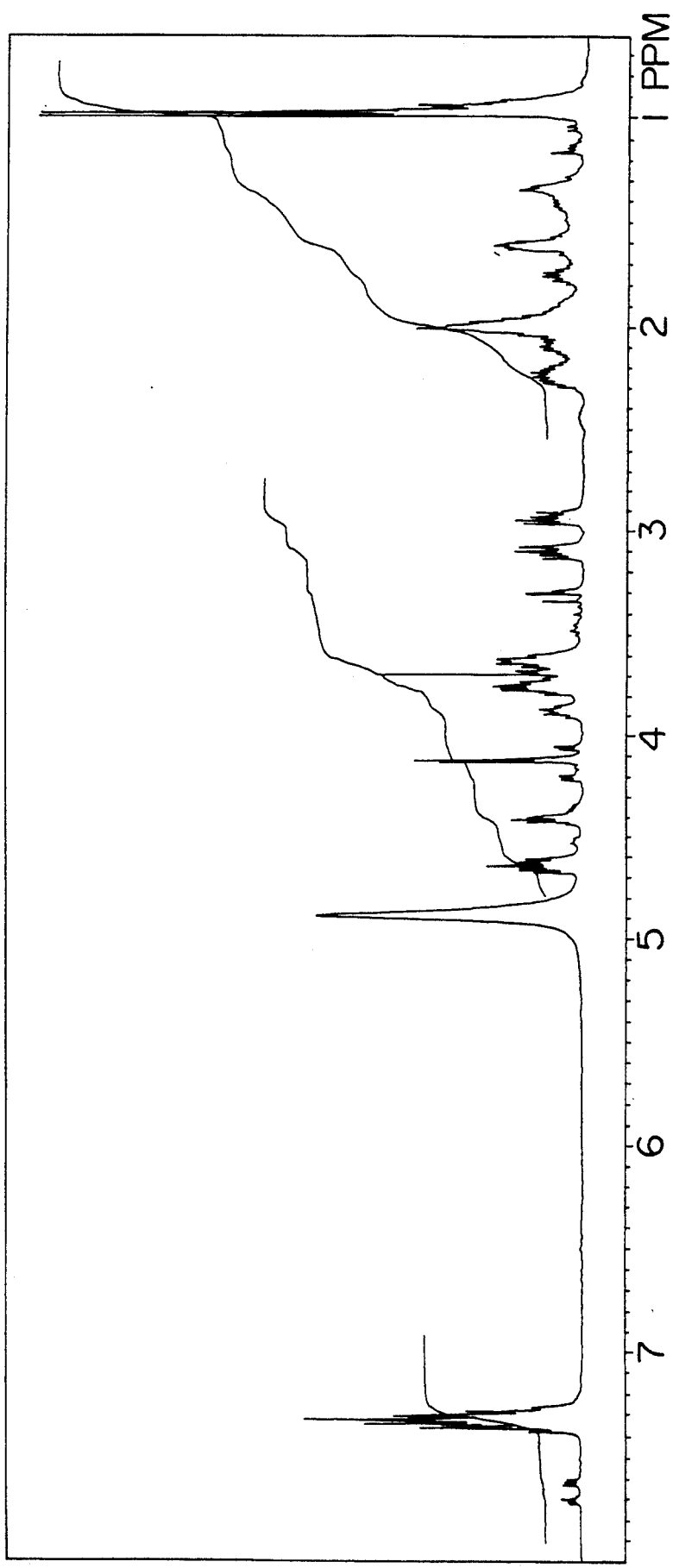

Probestin and prostatin have the following physicochemical properties:

(A) Physico-chemical properties of probestin (1) Color and Appearance:
 Colorless powder
(2) Empirical formula:
 $C_{26}H_{38}N_4O_6$
(3) Molecular weight as measured by SI-MS, m/z:
 502
(4) Melting point:
 168°-170° C.
(5) Specific optical rotation:
 $[\alpha]_D^{25} - 116.8°$ (c 1, methanol)
(6) Ultra-violet absorption spectrum:
 No characteristic absorption peak is observed in the range of 210 nm to 360 nm when determined in a solution of 1 mg/ml of probestin in methanol.
(7) Infrared absorption spectrum:
 As shown in FIG. 1 of the accompanying drawings.
(8) Proton nuclear magnetic resonance absorption spectrum ($^1$H-NMR):
 As shown in FIG. 2 of the accompanying drawings.
(9) Chemical shift in carbon nuclear magnetic resonance spectrum:
 As shown in Table 1 given hereafter.
(10) Color reaction:
 Positive reactions to ninhydrin and molybdenum-sulfuric acid reagents when tested on a silica-gel thin layer.
(11) Solubility:

Readily soluble in water, methanol and dimethyl-sulfoxide, but insoluble in acetone, ethyl acetate, chloroform and hexane.

(12) Rf values of thin layer chromatography:
  (i) Parallel phase chromatography [on Silica gel "Art. 5715" (Merck)];
  Rf=0.39
  when developed with n-butanol-acetic acid-water (4:1:1) as eluent.
  (ii) ODS-reversed phase chromatography [on Silica gel "Art. 15389" (Merck)];
  Rf=0.57
  when developed with acetonitrile-buffered solution A* (3:5) as eluent.

The buffered solution A* comprised an aqueous solution of 5% potassium acetate and 1% citric acid monohydrate.

(13) Distinction between basic, acidic and neutral natures: Neutral.

Figure 3:
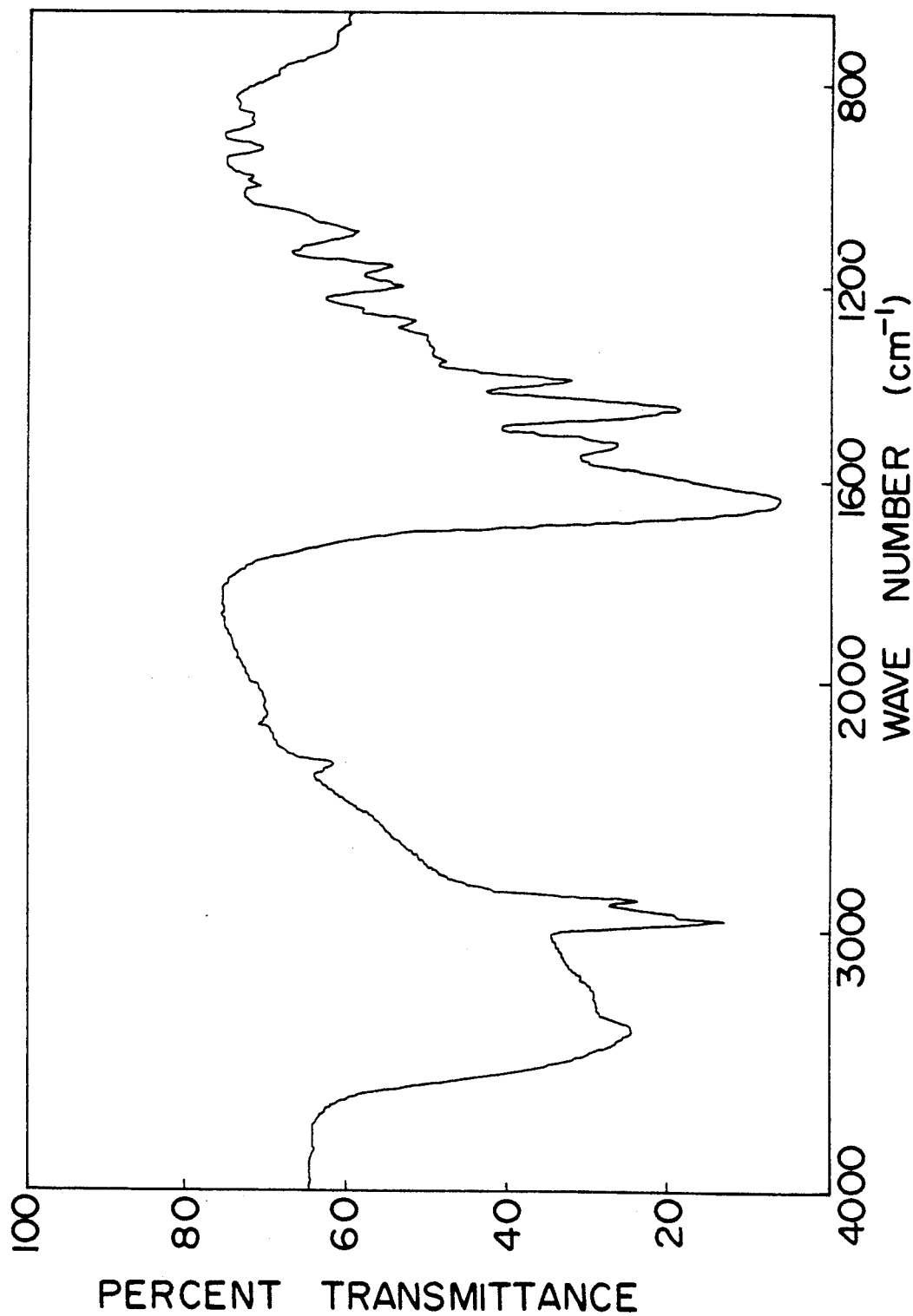
Figure 4:
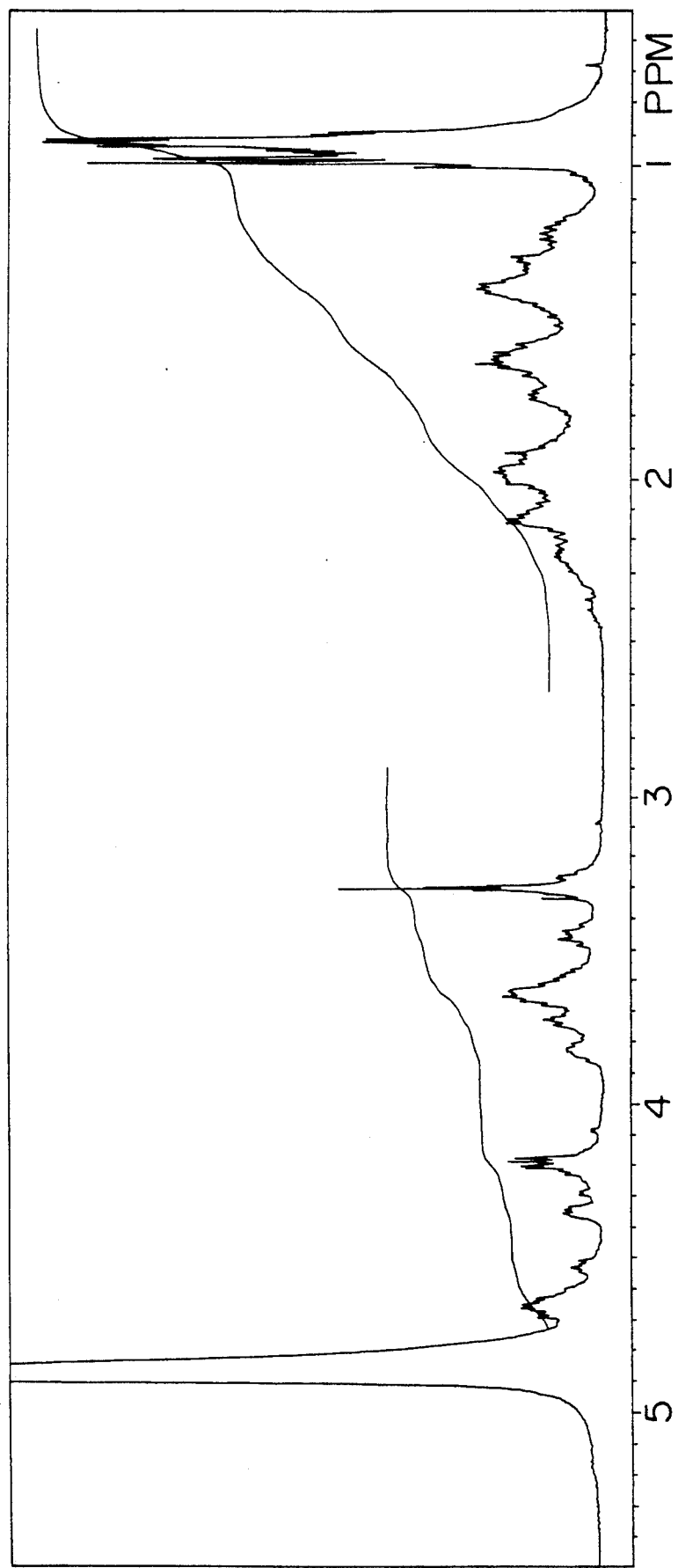

(B) Physico-chemical properties of prostatin ( (1) Color and appearance:
Colorless powder
(2) Empirical formula:
$C_{25}H_{44}N_4O_6$
(3) Molecular weight as measured by SI-MS, m/z: 496
(4) Melting point:
147°–150° C.
(5) Specific optical rotation:
$[\alpha]_D^{25} - 105.4°$ (c 1, methanol)
(6) Ultra-violet absorption spectrum:
No characteristic absorption peak is observed in the range of 210 nm to 360 nm when determined in a solution of 1 mg/ml of prostatin in methanol.
(7) Infrared absorption spectrum:
As shown in FIG. 3 of the accompanying drawings.
(8) Proton nuclear magnetic resonance absorption spectrum ($^1$H-NMR):
As shown in FIG. 4 of the accompanying drawings.
(9) Chemical shift in carbon nuclear magnetic resonance spectrum:
As shown in Table 1 given hereinafter.
(10) Color reaction:
Positive reactions to ninhydrin and molybdenum-sulfuric acid reagents when tested on a silica-gel thin layer.
(11) Solubility:
Readily soluble in water, methanol and dimethyl-sulfoxide, soluble in acetone and chloroform, but insoluble in ethyl acetate and hexane.
(12) Rf value of thin layer chromatography:
  (i) Parallel phase chromatography (on silica gel "Art. 5715" (Merck));
  Rf=0.41
  when developed with n-butanol-acetic acid-water (4:1:1) as eluent.
  (ii) ODS-reversed phase chromatography [on silica gel "Art. 15389" (Merck)];
  Rf=0.45
  when developed with acetonitrile-buffered solution A* (3:5) as eluent.

The buffered solution A* comprised an aqueous solution of 5% potassium acetate and 1% citric acid monohydrate.

(13) Distinction between basic, acidic and neutral natures:
Neutral.

The following Table 1 shows the chemical shifts in carbon nuclear magnetic spectra of probestin and prostatin as measured in deutro-methanol (100 MHz).

TABLE 1

| Probestin | | Prostatin | |
|---|---|---|---|
| 175.3 ppm | s | 173.8 ppm | s |
| 173.3 | s | 172.5 | s |
| 172.7 | s | 172.3 | s |
| 172.3 | s | 171.6 | s |
| 136.7 | s | 71.4 | d |
| 130.6 | d | 60.8 | d |
| 130.6 | d | 59.8 | d |
| 130.0 | d | 55.7 | d |
| 130.0 | d | 51.1 | d |
| 128.5 | d | 48.4 | t |
| 69.8 | d | 48.1 | t |
| 60.4 | d | 40.9 | t |
| 59.7 | d | 35.7 | d |
| 56.4 | d | 33.4 | t |
| 51.4 | d | 31.3 | t |
| 48.6 | t | 30.7 | t |
| 48.0 | t | 30.3 | t |
| 40.9 | t | 29.2 | t |
| 36.4 | t | 26.0 | d |
| 30.0 | t | 25.9 | t |
| 29.1 | t | 25.8 | t |
| 25.9 | d | 23.6 | q |
| 25.9 | t | 21.8 | q |
| 25.8 | t | 19.3 | q |
| 23.6 | q | 11.6 | q |
| 22.0 | q | | |

Note:
s: singlet
d: doublet
t: triplet
q: quinttet
Internal standard: tetramethylsilane Referring to the accompanying drawings:
FIG. 1 shows an infrared absorption spectrum of probestin pelleted in potassium bromide.
FIG. 2 shows a proton nuclear magnetic resonance absorption spectrum (400 MHz) of probestin in deuteromethanol.
FIG. 3 shows an infrared absorption spectrum of prostatin pelleted in potassium bromide, and
FIG. 4 shows a proton nuclear magnetic resonance absorption spectrum (400 MHz) of prostatin in deuteromethanol.

The activities of probestin and prostatin inhibitory to aminopeptidase M and other some aminopeptidases were assayed according to the method as described in the "Journal of Antibiotics" Vol. 38, pages 1629–1630 (1985); as detailed hereinafter.

The results of the assay are shown in Table 2 below;

TABLE 2

| | Value of IC$_{50}$ (μg/ml) against enzymes | | | |
|---|---|---|---|---|
| Inhibitors | Aminopeptidase M | Leucine-aminopeptidase | Aminopeptidase-A | Aminopeptidase-B |
| Probestin | 0.023 | 0.091 | >100 | 36.7 |
| Prostatin | 0.028 | 0.3 | 91.1 | 60.0 |
| Actinonin | 0.40 | 1.0 | >100 | >100 |

TABLE 2-continued

| | Value of $IC_{50}$ (μg/ml) against enzymes | | | |
|---|---|---|---|---|
| Inhibitors | Amino-peptidase M | Leucine-aminopeptidase | Amino-peptidase-A | Amino-peptidase-B |
| (reference) | | | | |

As apparent from Table 2 above, probestin and prostatin both exhibit a significantly and remarkedly higher activity inhibitory to aminopeptidase M, than that of actinonin.

Probestin and prostatin also show an immunopotentiating activity as will be clear from the following experiments.

Thus, the immunopotentiating activities of probestin and prostatin were assayed in respect of their ability to increase the number of antibody-forming cells in spleen which participate in the formation of antibody in the serum and hence the humoral immunity in mammalian animals. The effects of probestin and prostatin on the humoral antibody formation were assayed as follows: CDF-mice were immunized by intravenous injection of $10^8$ sheep red blood cells (SRBC). 1000 μg/mouse, 250 μg/mouse or 62.5 μg/mouse of probestin was administered by intraperitoneal injection into the mice at the time of the immunization with SRBC (0 hour) and then totally three times, namely 24, 48 and 72 hours after the immunization. Four days after the immunization with SRBC, the number of the plaque-forming cell (PFC) (namely, the antibody-forming cells) in spleen was enumerated by the known Jerne's hemolytic plaque technique [Jerne, N.K; A. A. Nordin & C. Henry; "The agar plaque technique for recognizing antibody-producing cells in cell-bound antibodies" pp. 109–122 published by Wister Institute press, Philadelphia (1963)].

The test results are shown in Table 3 below;

TABLE 3

| Test compound | Dose (μg/mouse) | Route of administration | Number of PFC ($\times 10^3$/spleen) | T/C (%) | P |
|---|---|---|---|---|---|
| Control | 0 | — | 232.100 | 100 | |
| Probestin | 1000 | ip. | 891.900 ± 162.610 | 384.1 | <0.001 |
| Probestin | 250 | ip. | 631.680 ± 69.560 | 271.8 | <0.001 |
| Probestin | 62.5 | ip. | 492.540 ± 69.980 | 212.1 | <0.001 |

As will be apparent from Table 3, intraperitoneal injections of probestin in a dose of 1000 μg to 62.5 μg/mouse led to an increased number of the antibody-forming cells in the spleen.

Prostatin was tested in the same way as above and it has been found that intraperitoneal injection of prostatin increased the number of the antibody-forming cells in spleen of the mice substantially as much as probestin. Accordingly, it has been found that both of probestin and prostatin are an immunopotentiator which arguments the immunity in mice and other mammalian animals. Therefore, probestin and prostatin according to this invention are useful as the immunopotentiator and are expectable to be useful as an immunopotentiating antitumor agent; since actinonin having an inhibitory activity against aminopeptidase M has been found to be useful as immunopotentiating antitumor agent (see U.S. Pat. No. 4,663,342).

Acute toxicity of probestin and prostatin were estimated by intravenous injection in mice, when it was found that probestin and prostatin each exhibited an $LD_{50}$ value of greater than 250 mg/kg.

According to a second aspect of this invention, there is provided a process for the production of a physiologically active substance, probestin, which comprises cultivating a probestin-producing strain of the genus Streptomyces under aerobic conditions in a culture medium containing assimilable carbon and nitrogen sources to produce and accumulate probestin in the culture, and recovering probestin from the culture.

According to a third aspect of this invention, there is provided a process for the production of a physiologically active substance, prostatin, which comprises cultivating a prostatin-producing strain of the genus Streptomyces under aerobic conditions in a culture medium containing assimilable carbon and nitrogen sources to produce and accumulate prostatin in the culture, and recovering prostatin from the culture.

As an example of the probestin-producing strain and prostatin-producing strain, there may be mentioned a strain of Streptomyces designated as MH663-2F6 strain, which was isolated by us from a soil sample collected in Shinagawa-ku, Tokyo. This MH663-2F6 strain has the following microbiological properties.

Microbiological properties of the MH663-2F6 strain

1. Morphological observations

The MH663-2F6 strain has branched substrate mycelia, from which aerial hyphae develop in the form of open spirals. No whirl-formation is observed. Matured spore chains usually bear more than 20 conical spores. Spores are measuring about 0.7–0.8 by 0.7–0.9 microns in size and have smooth surface.

2. Characteristics of the growth on various culture media

The designation of colors in brackets mentioned below follows the color standard given in the "Color Harmony Manual" published by Container Corporation of America.

(1) On sucrose-nitrate agar (incubated at 27° C.):
The growth is colored pale yellow [2ea, Lt. Wheat ~3 ca, Pearl Pink] and faintly develops colorless aerial hyphae. No soluble pigment is observed.

(2) On glycerol-nitrate agar (incubated at 27° C.):
Pale-yellow growth [2ca, Lt. Ivory~2ea, Lt. Wheat] develops yellowish gray aerial hyphae [2ba, Pearl~2cb, Ivory Tint]. No soluble pigment is observed.

(3) On glucose-asparagine agar (incubated at 27° C.):
Pale yellow growth [11/2gc, Dusty Yellow] faintly develops colorless aerial hyphae. No soluble pigment is observed.

(4) On yeast extract-malt extract agar (ISP - medium 2, incubated at 27° C.):

Pale yellow growth [2ea, Lt. Wheat] develops aerial hyphae of bright bluish gray color [17ec, Lt. Aqua Blue~19ec, Lt. Aqua Green]. No soluble pigment is observed.

(5) On oatmeal agar (ISP - medium 3, incubated at 27° C.):

The growth is pale yellow [2ba, Pearl] and develops aerial hyphae of bright bluish gray color [17ec, Lt. Aqua Blue]. No soluble pigment is observed.

(6) On inorganic salts-starch agar (ISP - medium 4, incubated at 27° C.):

The growth is colored pale yellow (2ba, Pearl) and develops aerial hyphae of bright bluish gray color [17ec, Lt. Aqua Blue]. No soluble pigment is observed.

(7) On glycerol-asparagine agar (ISP - medium 5, incubated at 27° C.):

The growth is colored pale yellow [2ea, Lt. Wheat] and faintly develops colorless aerial hyphae. No soluble pigment is observed.

(8) On tyrosine agar (ISP - medium 7, incubated at 27° C.):

The growth is colored pale olive [24ng, Leaf Green ~24 1/2 ng, Bright Olive Green] and develops aerial hyphae of bright bluish white color [17ca, Pale Aqua Blue]. Soluble pigment is faintly tinged with brown.

(9) On calcium malate agar (incubated at 27° C.):

The growth is colored pale yellow (2ba, Pearl) and develops aerial hyphae of bright bluish gray color [17ge, Dusty. Aqua Blue~19ge, Dusty Aqua Green]. No soluble pigment is observed.

(10) On nutrient agar (incubated at 27° C.):

The growth is colored pale yellowish brown [2gc, Bamboo] and develops aerial hyphae of white to yellowish brown color [2ba, Pearl]. Soluble pigment is faintly tinged with brown.

(11) On starch agar (incubated at 27° C.):

The growth is colored pale yellow [2ba, Pearl] and develops aerial hyphae of bright bluish gray color [17ec, Lt. Aqua Blue~19ec, Lt. Aqua Green]. No soluble pigment is observed.

(12) On skimmed milk (incubated at 37° C.):

The growth is colored pale brown [3gc, Lt. Tan] and develops no aerial hyphae. Soluble pigment of pale brown color is produced.

(13) On gelatin stab (incubated at 20° C.):

On the plain gelatin medium as incubated at 20° C., the growth is colored pale yellow [3ca, Pearl Pink] with faintly developing aerial hyphae of white color. No soluble pigment is observed.

On the glucose-peptone-gelatin medium as incubated at 27° C., the growth is colored pale brown [3gc, Lt. Tan], with faintly developing aerial hyphae of white color. Soluble pigment of dark brown color is produced.

(14) On cellulose (incubated at 27° C.):

The growth is colorless and faintly develops aerial hyphae of white color. No soluble pigment is observed.

3. Physiological properties (1) Temperature for growth

Growth on starch-yeast extract agar [yeast extract (a product of Daigo Eiyo Kagaku Co., Ltd.) 0.2%, soluble starch (a product of Komune Kagaku Co., Ltd.) 1.0%, agar 3.0%, pH 7.0] was examined at 20° C., 24° C., 27° C., 30° C. and 50° C. MH663-2F6 strain grew at all temperatures tested, but not at 50° C. Optimum temperature for good growth appeared to be in the range of 24° C. to 30° C.

(2) Liquefaction of gelatin

Plain gelatin (15%) medium did not start to liquefy when MH663-2F6 strain was incubated at 20° C. The glucose-peptone-gelatin medium started to liquefy from about the 15th day of incubation when MH663-2F6 strain was incubated at 27° C. The grade of liquefaction was then weak.

(3) Hydrolysis of starch

The starch in the inorganic salts-starch agar medium and in the starch-agar medium started to be hydrolyzed from about the 5th day of incubation when MH663-2F6 strain was incubated at 27° C., and the grade of hydrolysis was rather strong.

(4) Coagulation and peptonization of skimmed milk

When MH663-2F6 strain was incubated at 37° C., the skimmed milk (Difco) (10%) did not coagulate, but started to peptonize on the 15th day of incubation. The peptonization of skimmed milk was not finished in and after the 21st day of incubation. The grade of peptonization was weak.

(5) Formation of melanoid pigment

Pigmentation is observed on tryptone-yeast extract-broth (ISP-medium 1), and on peptone-yeast extract-iron agar (ISP-medium 6), but not on tyrosine agar (ISP-medium 7), when MH663-2F6 strain was incubated at 27° C. The grade of formation of melanoid pigment was strong on tryptone-yeast extract-broth and on peptone-yeast extract-iron agar.

(6) Utilization of carbon sources for growth

Utilization of the following carbohydrates was tested in Pridham-Gottlieb agar medium (ISP-medium 9) when MH663-2F6 strain was incubated at 27° C.

D-Glucose, L-arabinose, D-xylose, D-fructose, sucrose, inositol, L-rhamnose, raffinose and D-mannitol were utilized for growth.

(7) Liquefaction of calcium malate

When MH663-2F6 strain was incubated at 27° C., calcium malate in the calcium malate-agar medium was liquefied. The grade of liquefaction was medium to strong.

(8) Reduction of nitrate

Reduction of nitrate was positive when MH663-2F6 strain was incubated in an aqueous peptone solution containing 1.0% potassium nitrate (ISP-medium 8) at 27° C.

(9) Decomposition of cellulose

Decomposition of cellulose was negative when MH663-2F6 strain was incubated in a synthetic test solution containing paper pieces at 27° C.

Summarizing the above-mentioned properties of the MH663-2F6 strain, it is noted that this strain belongs to the genus Streptomyces and is essentially characterized in that the cell wall contains LL-type of 2,6-diaminopimelic acid.

The MH663-2F6 strain is also characterized in that the sporangium is not formed and its aerial hyphae develops open spirals but does not form the whirl, and that the surfaces of spore is smooth under microscopic observation.

On various culture media, the growth of the MH663-2F6 strain has a color of pale yellow, with developing aerial hyphae of white to bright bluish gray color. The soluble pigment is tinged with brown in the organic media, but is not produced in the other media. Production of melanoid pigment is positive on various media.

Proteolysis is rather weak, but starch hydrolysis is of strong grade.

On the basis of the above-mentioned characteristics of the MH663-2F6 strain, this strain has been compared to known analogous species of the genus Streptomyces, with reference to descriptions of some publications. It is found that the MH663-2F6 strain resembles to and is most closely related to *Streptomyces caelestis* [see publication 1: "International Journal of Systematic Bacteriology" Vol. 18, page 90 (1968), publication 2: S. A. Waksman "The Actinomycetes" Vol. 2, page 184 (1961), publication 3: R. Hutter "Systematik der Streptomyceten" page 89, (1967)] and *Streptomyces azureus* [see publication 1: "International Journal of Systematic Bacteriology" Vol. 18, page 87 (1968), publication 2: R. Hütter "Systematik der Streptomyceten" page 88, (1967)].

In this situation, we have compared the MH663-2F6 strain with the above-specified two strains of the genus Streptomyces which have been stored in the inventor's laboratory. The results of our comparison are summarized in Table 4 below;

TABLE 4

|  | MH663-2F6 | Streptomyces caelestis IMC S-0225 (ISP 5084) | Streptomyces azureus IMC S-0208 (ISP 5106) |
| --- | --- | --- | --- |
| Formation of spirals | + | + | + |
| Formation of whirls | — | — | — |
| Spore surface | Smooth | Smooth | Smooth |
| Color of aerial hyphae | White to bright bluish gray | White to bright bluish gray | White to grayish bluish green |
| Color of growth | Pale yellow to pale yellowish brown or pale brown | Pale yellowish brown to pale brown | Pale yellowish brown to pale brown |
| Soluble pigment | — ~ brownish color | — ~ brownish color | — ~ brownish color |
| Production of melanoid pigment |  |  |  |
| On ISP-medium 1 | + | + | + |
| On ISP-medium 6 | + | + | + |
| On ISP-medium 7 | — | — | — |
| Hydrolysis of starch | + | + | + |
| Coagulation of milk | — | — | — |
| Peptonization of milk | + (faint) | + (faint) | + (faint) |
| Liquefaction of gelatin |  |  |  |
| In plain gelatin medium | — | — | — |
| In glucose-peptone-gelatin medium | + | + | + |
| Reduction of nitrate | + | + | + |
| Utilization of carbon sources |  |  |  |
| L-Arabinose | + | + | + |
| D-Xylose | + | + | + |
| D-Glucose | + | + | + |
| D-Fructose | + | + | + |
| Sucrose | + | + | + |
| Inositol | + | + | + |
| L-Rhamnose | + | + | + |
| Raffinose | + | + | + |
| D-Mannitol | + | — | + |

As will be apparent from Table 4 above, the MH663-2F6 strain which may be used in this invention is closely related to *Streptomyces caelestis* and *Streptomyces azureus* in their microbiological properties.

The MH663-2F6 strain is different from *Streptomyces caelestis* only in the utilization of D-mannitol, and it is different from *Streptomyces azureus* in respect of the color characteristics of aerial hyphae. Thus, *Streptomyces azureous* develops the aerial hyphae with a color of much more thicker bluish green, as compared with that of the MH663-2F6 strain. The development of open spirals in the aerial hyphae which is one of the morphological characteristics of the MH663-2F6 strain is also equally observed with *Streptomyces azureus*, as described in the abovementioned "International Journal of Systematic Bacteriology" and R. Hütter's publication and also has been confirmed by our actual comparative experiments. It appears at a glance under microscopic observation that the MH663-2F6 strain and *S. azureus* both form whirl with open spirals. On the other hand, *Streptomyces caelestis* produces poorly open spirals, with the open spirals having 1–2 turns and with the spore chains being short.

Accordingly, it has been estimated that the MH663-2F6 strain belongs to *Streptomyces azureus*, and is designated as *Streptomyces azureus* MH663-2F6.

This MH663-2F6 strain has been deposited in the Japanese depository "Fermentation Research Institute, Agency of Industrial Science and Technology" at Address No. 1-3, Higashi 1-chome, Tsukuba-shi, Ibaraki-Ken, 305, Japan, since Aug. 27, 1987 under deposit number FERM P-9541 and now deposited there under accessible number FERM BP-1963 in terms of the Budapest Treaty.

Mutation of Streptomyces occurs frequently in either artificial or spontaneous conditions, and accordingly this invention includes the use of the MH663-2F6 strain as well as its mutants. In other words, this invention includes in its scope the use of such mutants of the MH663-2F6 strain which have been induced spontaneously or artificially, in particular by the techniques of fusion or recombination of genes of the MH663-2F6 strain, as long as such mutants are capable of producing probestin and/or prostatin.

In carrying out the process according to the second aspect or the third aspects of this invention, an amount of the probestin-producing strain or the prostatin-producing strain of the genus *Streptomyces*, typically *Streptomyces azureus* MH663-2F6 strain (identified as FERM P-9541 or FERM BP-1963) is inoculated to a suitable culture medium comprising assimilable carbon and nitrogen sources and is then incubated under aerobic conditions, preferably under submerged aerobic conditions, so that probestin and/or prostatin is (are) produced and accumulated in the culture broth. Commercially available carbohydrates such as glucose, glutinous starch syrup, dextrin, sucrose, starch and molasses, as well as fats and oils of animals or plants are useful as the carbon sources. Commercially available soybean meal, wheat embryo, corn steep liquor, cotton seed meal, meat extract, poptone, yeast extract, ammonium sulfate, ammonium nitrate, urea and the like may be useful as the nitrogen sources. In addition, one or more inorganic salts which give sodium cation, cobalt cation, chloride anion, phosphate anion, sulfate anion, and other ions may effectively be employed as the salt additive in the culture medium. Any of the organic and inorganic materials which promote the growth of the prostatin-producing strain or the probestin-producing strain employed, as well as the production of prostatin and/or probestin may also advantageously be employed as the additive in the culture medium.

For the production of probestin or prostatin, the cultivation of the microbial strain employed may suitably be effected under aerobic conditions, and submerged aerobic cultivation is preferred. A preferred cultivation temperature for the production of probestin or prostatin is in the range of 15° to 37° C., especially in the range of 26° to 30° C.

The production of probestin and prostatin can be achieved suitably by cultivation of the microorganism in a tank-fermentor or by shake-cultivation. In these methods of the cultivation, production and accumulation of probestin or prostatin in the culture reaches a maximum within 10 days of the cultivation. When the accumulation of probestin and/or prostatin in the culture reaches a maximum, the cultivation is stopped, followed by recovery of probestin and/or prostatin from the culture broth and purification of these desired substances. For recovery of probestin and prostatin from the culture broth, it is possible to use any conventional methods such as organic solvent-extraction, adsorption, precipitation and a combination thereof, with utilizing the properties of probestin and prostatin. Thus, the culture broth filtrate may be passed through a column of an adsorbent resin, "Amberlite" XAD-4 (a product of Organo Co. Japan) so that probestin and/or prostatin are adsorbed to the resin, and the resin may be washed with water and subsequently eluted with an organic solvent such as methanol. The resulting eluate may be distilled to remove the organic solvent therefrom. The residue obtained is extracted at pH 2 with an appropriate water-immiscible organic solvent such as butanol, so that the active ingredients can be extracted and recovered into butanol. The resultant extract in butanol may then be concentrated to dryness under a reduced pressure to give a crude powder comprising probestin and/or prostatin.

Subsequently, the isolation of probestin and prostatin from each other may be achieved by subjecting said crude powder to chromatography on an adsorbent, and gel filtration chromatography, either in proper combination or by repetition thereof.

When the aforesaid *Streptomyces azureus* MH663-2F6 strain is used as the probestin-producing strain or the prostatin-producing strain in the process according to the second or third aspect of this invention, probestin and prostatin are concurrently produced and accumulated in the culture broth. In a further aspect, therefore, this invention provides a process for the production of probestin and prostatin, which comprises cultivating *Streptomyces azureus* MH663-2F6 in a culture medium containing assimilable carbon and nitrogen sources, under aerobic conditions at a temperature of 20° C. to 37° C. to produce and accumulate probestin and prostatin in the culture, and recovering probestin and prostatin from culture. This process of the invention may be conducted in the same manner as described for the processes of the second and third aspects of this invention. Probestin and prostatin may be recovered from the culture broth as a mixture thereof and then may be isolated from each other and purified through a chromatographic method as described hereinbefore.

The assay of probestin or prostatin which is made in the course of cultivation of the probestin-producing strain or the prostatin-producing strain, as well as in the course of recovery and purification of probestin or prostatin may be conducted by determining the potency of probestin or prostatin inhibitory to aminopeptidase M according to the following procedure:

Thus, the assay of probestin or prostatin for its potency inhibitory to aminopeptidase M may be conducted according to the method of Umezawa et al. as described in the "Journal of Antibiotics" 38, 1629–1630 (1985). In detail, 0.25 ml of 2 mM aqueous L-leucine-$\beta$-naphthylamide (as substrate) and 0.5 ml of 0.1 M tris-hydrochloride buffered solution (pH 7.0) are added to 0.2 ml of an aqueous solution containing probestin or prostatin as test compound. The mixture solution obtained is heated at 37° C. for 3 minutes. To the heated solution is added 0.05 ml of an aqueous solution of aminopeptidase M (a product of Boehringer Mannheim Company; 4 units/mg). The resulting mixture is incubated for 30 minutes at 37° C. for the enzymatic reaction and the resultant reaction mixture is admixed with 1 ml of 1.0 M acetate buffered solution (pH 4.2) containing 10% of a surfactant "Tween" 20 and 0.1% of Fast Garnet GBC (0-aminoazotoluene, diazonium salt) to stop the enzymatic reaction. After allowing the resulting mixture to stand at ambient temperature for 15 minutes, the absorbance of light at 525 nm of the resultant reaction solution is measured, with designating the measured value as value (a). Concurrently, the absorbance of light at 525 nm of such a "control" reaction solution as obtained from the blank test where the enzymatic reaction is effected without probestin nor prostatin is measured, with designating the measured value as value (b). The rate (%) of inhibition to the aminopeptidase M is calculated from an equation $[(b-a)/b] \times 100$.

The production of probestin and prostatin is now illustrated with reference to the following Examples.

EXAMPLE 1

(a) As the culture medium for use in the preparation of the seed culture of the probestin or prostatin-producing microorganism, and as the culture medium for use in the fermentative production of probestin and prostatin was employed such culture medium comprising 2.0% potato starch, 2.0% glucose, 2.0% Soya meal, 0.5% yeast extract, 0.25% sodium chloride, 0.32% calcium carbonate, 0.0005% copper sulfate penta-hydrate, 0.005% manganese chloride tetrahydrate and 0.005% zinc chloride hepta-hydrate. The culture medium employed had been adjusted to pH 7.4 before sterilization.

The culture medium for preparation of the seed culture was dispensed in 110 ml-portions into 500 ml conical flasks and then was sterilized by heating at 120° C. for 20 minutes. One to two loopful quantity of the mycelia harvested from a slant culture of *Streptomyces azureus* MH663-2F6 (identified as FERM P-9541 or FERM BP-1963) were inoculated in the sterilized culture medium prepared as above, and the inoculated culture medium was incubated at 28° C. for 2 days under agitation, so that a first seed culture was afforded. 3 ml-portions of the first seed culture obtained were inoculated into further volumes of the culture medium for preparation of the seed culture which had been dispensed in 110 ml-portions into five 500 ml conical flasks and sterilized at 120° C. for 20 minutes. The so inoculated culture medium was then incubated at 28° C. for 2 days under agitation, so that a second seed culture was afforded. 500 ml-portions of the second seed culture obtained were inoculated into the productive culture medium which had been placed in 12 l-portions into 30 l Jar-fermentors and sterilized at 120° C. for 20 minutes. The inoculated productive culture medium was incubated at 28° C. for 48 hours under aeration (12 l of air per minute) and with agitation (150 rpm).

After the completed incubation, the culture broth was admixed with a filter aid (diatomaceous earth) and the mixture was filtered to give the culture broth filtrate and a filter cake containing the mycelium.

(b) The culture broth filtrate (10 l) obtained in the above step (a) was passed into a column of 1 l of an adsorbent resin "Amberlite" XAD-4. The "Amberlite" column was then washed with water and subsequently eluted with 80% aqueous methanol (4 l). The fractions of the eluate containing the active ingredients were collected, combined and concentrated under reduced pressure to a volume of 300 ml. The concentrate obtained was adjusted to a pH 2.0 with hydrochloric acid, and then admixed with 300 ml of butanol, followed by vigorous agitation. The resulting extract in butanol was concentrated under reduced pressure to obtain 3.6 g of a brown colored crude material containing probestin and prostatin.

(c) The crude material obtained in the above step (b) was suspended in a small volume of a solvent mixture of butyl acetate, butanol, acetic acid and water (2:4:1:1). The suspension was passed into a column of 300 ml of Silica gel ("Wako Gel" C-200, a product of Wako Junyaku Co., Japan) which had been packed with the same solvent mixture as mentioned above. The silica gel column was then eluted with a further volume of the same solvent mixture. The eluate was concentrated under reduced pressure to obtain 320 mg of a pale brown colored crude powder.

(d) The crude powder obtained in the above step (c) was dissolved in water, and the aqueous solution was subjected to a reversed phase column chromatography on a column of a silanized silica gel (70 ml) ("Silanized silica gel" 60, a product of Merck Co., U.S.A.) which had been packed with water. This column was then eluted gradiently with 0 to 50% aqueous methanol. In this gradient elution procedure, the eluate was collected in 7 g-fractions. Probestin was eluted in Fractions Nos. 51-70, while prostatin was eluted in Fraction Nos 81-96.

(e) The eluate fractions predominantly containing probestin, as obtained in the step (d), were combined and concentrated under reduced pressure to give 55.9 mg of a yellowish powder This powder was dissolved in a small volume of methanol, and the solution was subjected to a column chromatography on 500 ml of an adsorbent resin, "Toyopel" HW-40 (a product of Toyo Soda Kogyo Co., Ltd.) which was packed with methanol. The resin column was then eluted chromatographically with methanol. The eluate was collected in 3 g-fractions. The active fractions (fraction Nos 67 to 70) of the eluate were combined and concentrated under reduced pressure to afford 30.5 mg of a pure probestin as a colorless powder. This probestin powder showed an inhibitory potency of $IC_{50}$ of 0.023 μg/ml against aminopeptidase M.

(f) The eluate fractions predominantly containing prostatin, as obtained in the step (d), were combined and concentrated under reduced pressure to obtain 14.0 mg of a yellowish powder. This powder was dissolved in a small volume of a solvent mixture of methanol and water (1:1), and the solution was subjected to a column chromatography on "Sephadex" LH-20 (700 ml) (a product of Pharmacia Fine Chemical Co., Sweden) which was packed with a solvent mixture of methanol and water (1:1). This column was then eluted chromatographically with a solvent mixture of methanol and water (1:1), with the eluate being collected in 5 g-fractions.

The active fractions fraction Nos. 29 to 34) were combined and concentrated under reduced pressure to afford 6.8 mg of a pure prostatin as a colorless powder. This prostatin powder showed an inhibitory potency of $IC_{50}$ of 0.028 μg/ml against aminopeptidase M.

We claim:

1. A substance selected from probestin and prostatin which are represented by the following formula;

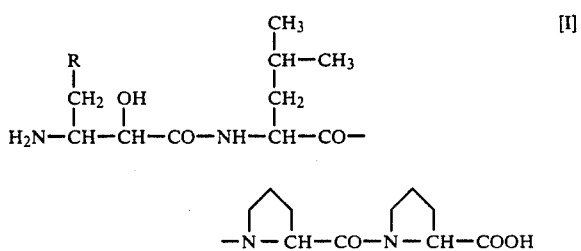

wherein R denotes a phenyl group for probestin, or R denotes a 2-methyl-butyl group for prostatin, or a pharmaceutically acceptable salt thereof.

2. A physiologically active substance of claim 1, which is probestin, represented by the formula;

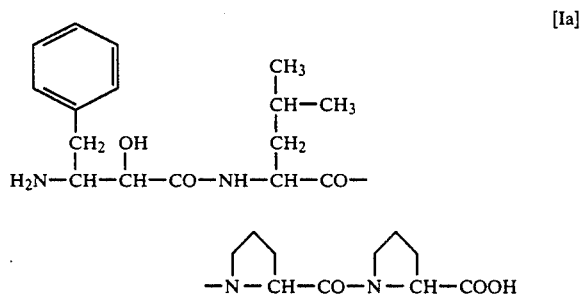

3. A physiologically active substance of claim 1, which is prostatin, represented by the formula;

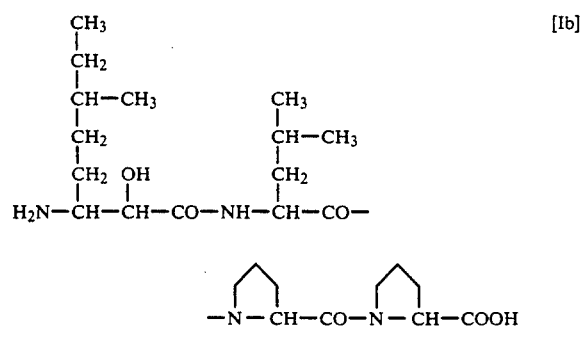

* * * * *